(12) United States Patent
Hallinan et al.

(10) Patent No.: US 9,102,612 B2
(45) Date of Patent: Aug. 11, 2015

(54) PROCESS FOR THE PRODUCTION OF ACETIC ACID

(75) Inventors: Noel C. Hallinan, Loveland, OH (US); Brian A Salisbury, Oxford, PA (US); Wayne J Brtko, Cincinnati, OH (US); Michael E Fitzpatrick, League, TX (US)

(73) Assignee: LyondellBasell Acetyls, LLC, Houston, TX (US)

( * ) Notice: Subject to any disclaimer, the term of this patent is extended or adjusted under 35 U.S.C. 154(b) by 277 days.

(21) Appl. No.: 13/531,987

(22) Filed: Jun. 25, 2012

(65) Prior Publication Data

US 2013/0345474 A1    Dec. 26, 2013

(51) Int. Cl.
*C07C 51/12* (2006.01)
*C07C 51/50* (2006.01)

(52) U.S. Cl.
CPC ................. *C07C 51/50* (2013.01); *C07C 51/12* (2013.01)

(58) Field of Classification Search
CPC ............................... C07C 51/12; C07C 51/50
See application file for complete search history.

(56) References Cited

U.S. PATENT DOCUMENTS

| 5,817,869 A | 10/1998 | Hinnenkamp et al. | |
| 5,932,764 A | 8/1999 | Morris et al. | |
| 6,031,129 A * | 2/2000 | Hinnenkamp et al. | 562/519 |
| 6,552,221 B1 | 4/2003 | Hallinan et al. | |
| 8,076,508 B2 | 12/2011 | Brtko et al. | |
| 2005/0176996 A1 | 8/2005 | Law et al. | |
| 2008/0269519 A1 | 10/2008 | Miller et al. | |
| 2011/0009665 A1* | 1/2011 | Scates | 562/519 |
| 2011/0054213 A1 | 3/2011 | Fitzpatrick et al. | |
| 2011/0313217 A1 | 12/2011 | Hallinan et al. | |

OTHER PUBLICATIONS

Hallinan et al, Catalysis of Organic Reactions, Rhodium Catalyzed Methanol Carbonylation: New Low Water Technology, 2000, Marcel Dekker, Inc., New York, pp. 545-556.*
Zaragoza Dorwald, Side Reactions in Organic Synthesis, 2005, Wiley-VCH Verlag GmbH & Co. KGaA, Weinheim, Preface. p. IX.*
White et al, Basic Energy Sciences Advisory Committee Subpanel Workshop Report, Opportunities for Catalysis in the 21st Century, 2002, pp. 1-47.*
PCT/US2013/047085 International Search Report and Written Opinion mailed Oct. 18, 2013.
Noel Hallinan & James Hinnenkamp, "Rhodium Catalyzed Methenol Carbonylation: New Low Water Technology" Catalyst of Organic Reactions, pp. 545-556 (Michael E. Ford) ed. 2000. US.
Jane. H. Jones, "The CATIVA Process for the Manufacture of Acetic Acid", 44 (3) Platinum Metals Rev. 94-105 (2000). US.
Jones, Roberts and Taylor, "C1 to Acetyls: Catalysis and Process", 18 Catalysis Today 325-354 (1993). US.

* cited by examiner

*Primary Examiner* — Paul A Zucker

(57) ABSTRACT

A process for producing acetic acid includes: obtaining hydrogen iodide in an acetic acid production system; and continually introducing a complexing agent into the system, wherein the complexing agent and hydrogen iodide interact to form a complex.

18 Claims, 4 Drawing Sheets

US 9,102,612 B2

PROCESS FOR THE PRODUCTION OF ACETIC ACID

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND

1. Field of the Invention

The disclosure relates to the production of acetic acid. More particularly, the disclosure relates to management of hydrogen iodide ("HI") levels in acetic acid production.

2. Related Art

This section introduces information from the art that may be related to or provide context for some aspects of the technique described herein and/or claimed below. This information is background facilitating a better understanding of that which is disclosed herein. This is a discussion of "related" art. That such art is related in no way implies that it is also "prior" art. The related art may or may not be prior art. The discussion is to be read in this light, and not as admissions of prior art.

Production of acetic acid by methanol carbonylation is known. In the current acetic acid production process, a reaction mixture is withdrawn from a reactor and is separated in a flash tank into a liquid fraction and a vapor fraction comprising acetic acid generated during the carbonylation reaction. The liquid fraction may be recycled to the carbonylation reactor, and the vapor fraction is passed to a separations unit, which by way of example may be a light-ends distillation column. The light-ends distillation column separates a crude acetic acid product from other components. The crude acetic acid product is passed to a drying column to remove water and then is subjected to further separations to recover acetic acid.

Hydrogen iodide can be a reaction component in the production of acetic acid. Although process equipment generally used in the production of acetic acid is substantially inert to the reaction components, the equipment can still be corroded or otherwise adversely affected by HI. Additionally, HI can lead to the formation of long-chain alkyl iodide impurities, e.g., hexyl iodide, which are difficult to remove and which may complicate the recovery of acetic acid. Thus, the presence of HI can have consequences both in terms of corrosion of processing equipment and in terms of contamination of a final acetic acid product.

An improved acetic acid production process is thus needed which better manages levels of HI.

SUMMARY

In various aspects and embodiments, the claimed subject matter includes a process for producing acetic acid comprising: obtaining hydrogen iodide in an acetic acid production system; and continually introducing a complexing agent into the system, wherein the complexing agent and hydrogen iodide interact to form a complex. In another, the claimed subject matter includes an acetic acid product produced by such a method.

The above paragraph presents a simplified summary of the presently disclosed subject matter in order to provide a basic understanding of some aspects thereof. The summary is not an exhaustive overview, nor is it intended to identify key or critical elements to delineate the scope of the subject matter claimed below. Its sole purpose is to present some concepts in a simplified form as a prelude to the more detailed description set forth below.

BRIEF DESCRIPTION OF THE DRAWINGS

The claimed subject matter may be understood by reference to the following description taken in conjunction with the accompanying drawings, in which like reference numerals identify like elements, and in which:

While the claimed subject matter is susceptible to various modifications and alternative forms, the drawings illustrate specific embodiments herein described in detail by way of example. It should be understood, however, that the description herein of specific embodiments is not intended to limit the claimed subject matter to the particular forms disclosed, but on the contrary, the intention is to cover all modifications, equivalents, and alternatives falling within the spirit and scope of the invention as defined by the appended claims.

DETAILED DESCRIPTION

A detailed description of embodiments of the disclosed process follows. However, it is to be understood that the described embodiments are merely exemplary of the process and that the process may be embodied in various and alternative forms of the described embodiments. Therefore, specific procedural, structural and functional details which are addressed in the embodiments described herein are not to be interpreted as limiting, but merely as a basis for the claims and as a representative basis for teaching one skilled in the art to variously employ the disclosed process.

In the disclosure that follows, the designation of groups of the Periodic Table of the Elements as used herein is in accordance with the current IUPAC convention. Unless specifically indicated otherwise, the expression "wt %" as used herein refers to the percentage by weight of a particular component in the referenced composition. The expressions "OAc" or "AcO" are used herein as abbreviations for the acetate anion, i.e., $H_3CC(=O)O^-$. The expression "acac" is used herein as an abbreviation for acetoacetate anion, i.e., $H_3CC(=O)CH_2C(=O)O^-$. Finally, with respect to all ranges disclosed herein, such ranges are intended to include any combination of the mentioned upper and lower limits even if the particular combination is not specifically listed.

Embodiments of the disclosed process and system involve the production of acetic acid by carbonylating methanol in a carbonylation reaction. The carbonylation reaction may be represented by:

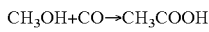
$$CH_3OH + CO \rightarrow CH_3COOH$$

Figure 1:
FIG. 1 sets forth some of the interrelated reactions and equilibria believed to be involved in the carbonylation of methanol in the presence of a rhodium catalyst.
Figure 1:
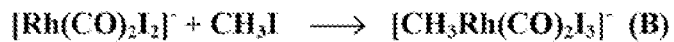
Figure 1:
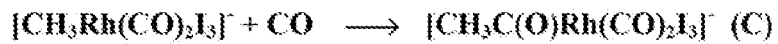
Figure 1:
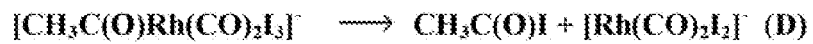
Figure 1:
Figure 1:
Figure 1:
Figure 1:
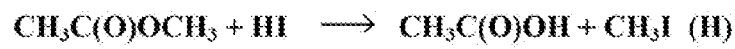

The underlying chemistry involves a multiplicity of interrelated reactions, by-products, and equilibria. FIG. 1 sets forth some of the interrelated reactions and equilibria believed to be involved in the carbonylation reaction. As can be seen in FIG. 1, HI may be a component in the underlying chemistry for the production of acetic acid.

Embodiments of the disclosed process generally include (a) obtaining HI in an acetic acid production system; and (b) continually introducing a complexing agent into the system, wherein the complexing agent and HI interact to form a complex. In this context, the term "continually" means introducing the complexing agent sufficiently frequently and in metered amounts to bring about steady state HI scavenging operations. This will eliminate large swings in the efficiency of scavenging operations produced in conventional practice by occasional introduction of large amounts of complexing agent. The following description shall elaborate upon the disclosed process in detail.

Figure 2:
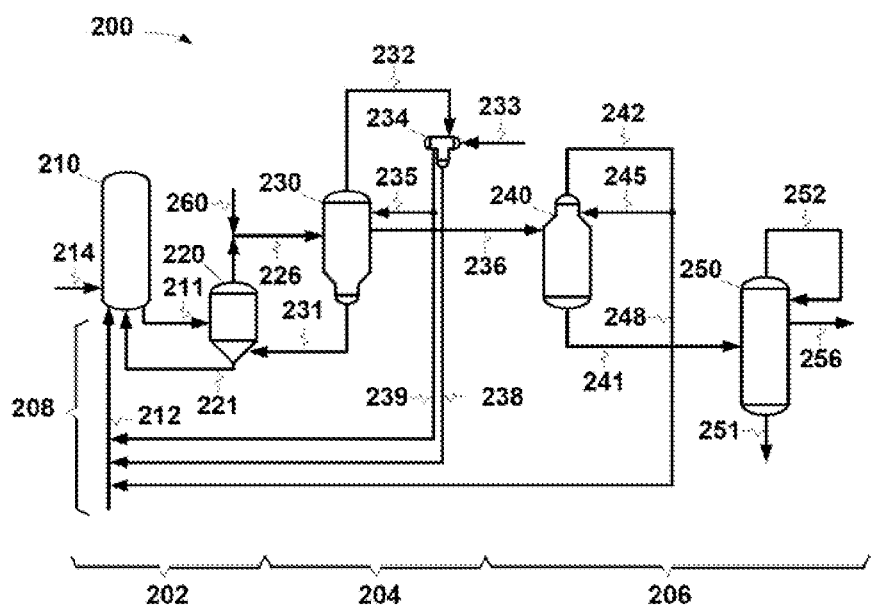
FIG. 2 illustrates a schematic of embodiments of the disclosed process.

FIG. 2 shows a schematic of an embodiment of an acetic acid production system 200 implementing the carbonylation reaction. In an embodiment, the acetic acid system 200 may be described in functional areas, i.e., a reaction area 202, a light-ends area 204, a purification area 206, and a recycle area 208. Note that the "streams" discussed herein may be part of more than one functional area.

The reaction area 202 may comprise a reactor 210, a flash vessel 220, equipment associated with the reactor 210 and flash vessel 220, and streams associated with the reactor 210 and flash vessel 220. For example, the reaction area 202 may comprise reactor 210, flash vessel 220, and streams (or portions of streams) 211, 212, 214, 221, 226, 231, 260, 238, 239, 248. The reactor 210 is a reactor or vessel in which methanol is carbonylated in the presence of a catalyst to form acetic acid at elevated pressure and temperature. The flash vessel 220 is a tank or vessel in which a reaction mixture obtained in the reactor, for example the reactor 210, is at least partially depressurized and/or cooled to form a vapor stream and a liquid stream. A vapor stream is a product or composition which comprises components in the gaseous state under the conditions of the processing step in which the stream is formed. A liquid stream may be a product or composition which comprises components in the liquid state under the conditions of the processing step in which the stream is formed.

The light-ends area 204 may comprise a separations column, for example a light-ends column 230, equipment associated with light-ends column 230, and streams associated with the light-ends column 230. For example, the light-ends area 204 may comprise light-ends column 230, decanter 234, and streams 226, 231, 232, 233, 235, 236, 238, 239, 260. The light-ends column 230 is a fractioning or distillation column and includes any equipment associated with the column, including but not limited to heat exchangers, decanters, pumps, compressors, valves, and the like.

The purification area 206 may comprise a drying column 240, optionally, a heavy-ends column 250, equipment associated with drying column 240 and heavy-ends column 250, and streams associated with the drying column 240 and heavy-ends column 250. For example, the purification area 206 may comprise drying column 240, heavy-ends column 250, and streams 236, 241, 242, 245, 248, 251, 252, 256. The heavy-ends column 250 is a fractioning or distillation column and includes any equipment associated with the column, including but not limited to heat exchangers, decanters, pumps, compressors, valves, and the like.

The recycle area 208 may comprise process streams recycled to the reaction area 202 and/or light-ends area 204. For example, in FIG. 2, the recycle area 208 may comprise streams 221, 238, 239, 248.

In an embodiment, the reactor 210 may be configured to receive a carbon monoxide feed stream 214 and a feed stream 212. The feed stream 212 may comprise a methanol feed stream, a methyl acetate feed stream or any mixture of the two. In the illustrated embodiment, the feed stream 212 is a mixed stream. A reaction mixture may be withdrawn from the reactor in stream 211. Other streams may be included as known in the art, for example, a stream that may recycle a bottoms mixture of the reactor 210 back into the reactor 210, or a stream may be included to release a gas from the reactor 210. Stream 211 may comprise at least a part of the reaction mixture.

In an embodiment, the flash vessel 220 may be configured to receive stream 211 from the reactor 210. In the flash vessel 220, stream 211 may be separated into a vapor stream 226 and a liquid stream 221. The vapor stream 226 may be fed to the light-ends column 230, and the liquid stream 221 may be recycled to the reactor 210 (stream 221 may thus be considered in the recycle area 208 and in the reactor area 202). In an embodiment, stream 226 may comprise acetic acid, water, methyl iodide, methyl acetate, HI, and mixtures thereof.

In an embodiment, the light-ends column 230 may comprise a distillation column and equipment associated with the distillation column including but not limited to a heat exchanger, a decanter 234, pumps, compressors, valves, and other related equipment. The light-ends column 230 may be configured to receive stream 226 from the flash vessel 220. Stream 232 comprises overhead product from the light-ends column 230, and stream 231 comprises bottoms product from the light-ends column 230. Light-ends column 230 may comprise a decanter 234, and stream 232 may pass into decanter 234.

Stream 235 may emit from decanter 234 and recycle back to the light-ends column 230. Stream 238 may emit from decanter 234 and may recycle back to the reactor 210 via, for example, stream 212 or be combined with any of the other streams that feed the reactor (stream 238 may thus be considered in the recycle area 208, in the light-ends area 204, and in the reactor area 202). Stream 239 may recycle a portion of the light phase of decanter 234 back to the reactor 210 via, for example, stream 212 (stream 239 may thus be considered in the recycle area 208, in the light-ends area 204, and in the reactor area 202). Stream 236 may emit from the light-ends column 230. Other streams may be included as known in the art, for example, a stream that may recycle a bottoms mixture of the light-ends column 230 back into the light-ends column 230. Any stream received by or emitted from the light-ends column 230 may pass through a pump, compressor, heat exchanger, and the like as is common in the art.

In an embodiment, the drying column 240 may comprise a vessel and equipment associated with the vessel including but not limited to heat exchangers, decanters, pumps, compressors, valves, and the like. The drying column 240 may be configured to receive stream 236 from the light-ends column 230. The drying column 240 may separate components of stream 236 into streams 242 and 241.

Stream 242 may emit from the drying column 240, recycle back to the drying column via stream 245, and/or recycle back to the reactor 210 through stream 248 (via, for example, stream 212). Stream 241 may emit from the drying column 240 and may comprise de-watered crude acetic acid product. Stream 242 may pass through equipment known in the art, for example, a heat exchanger or separation vessel before streams 245 or 248 recycle components of stream 242. Other streams may be included as known in the art, for example, a stream may recycle a bottoms mixture of the drying column 240 back into the drying column 240. Any stream received by or emitted from the drying column 240 may pass through a pump, compressor, heat exchanger, separation vessel, and the like as is common in the art.

The heavy-ends column 250 may comprise a distillation column and equipment associated with the distillation column including but not limited to heat exchangers, decanters, pumps, compressors, valves, and the like. The heavy-ends column 250 may be configured to receive stream 241 from the drying column 240. The heavy-ends column 250 may separate components from stream 241 into streams 251, 252, and 256. Streams 251 and 252 may be sent to additional processing equipment (not shown) for further processing. Stream 252 may also be recycled, for example, to light-ends column 240. Stream 256 may comprise acetic acid product.

Suitable alternative embodiments for the acetic acid production system 200 may be found in U.S. Pat. No. 6,552,221, which is herein incorporated by reference.

In an embodiment, the carbonylation reaction in reactor 210 of system 200 may be performed in the presence of a catalyst. Suitable catalysts include, for example, rhodium catalysts and iridium catalysts.

Suitable rhodium catalysts are taught, for example, by U.S. Pat. No. 5,817,869, which is herein incorporated by reference. Suitable rhodium catalysts may include rhodium metal and rhodium compounds. In an embodiment, the rhodium compounds may be selected from the group consisting of rhodium salts, rhodium oxides, rhodium acetates, organo-rhodium compounds, coordination compounds of rhodium, the like, and mixtures thereof. In an embodiment, the rhodium compounds may be selected from the group consisting of Rh2(CO)4I2, Rh2(CO)4Br2, Rh2(CO)4Cl2, Rh(CH3CO2)2, Rh(CH3CO2)3, [H]Rh(CO)2I2, the like, and mixtures thereof. In an embodiment, the rhodium compounds may be selected from the group consisting of [H]Rh(CO)2I2, Rh(CH3CO2)2, the like, and mixtures thereof.

Suitable iridium catalysts are taught, for example, by U.S. Pat. No. 5,932,764. Suitable iridium catalysts may include iridium metal and iridium compounds. Examples of suitable iridium compounds include IrCl3, IrI3, IrBr3, [Ir(CO)2I]2, [Ir(CO)2Cl]2, [Ir(CO)2Br]2, [Ir(CO)4I2]-H+, [Ir(CO)2Br2]-H+, [IR(CO)2I2]-H+, [Ir(CH3)I3(CO)2]-H+, Ir4(CO)12, IrCl3.4H2O, IrBr3.4H2O, Ir3(CO)12, Ir2O3, IrO2, Ir(acac)(CO)2, Ir(acac)3, Ir(OAc)3, [Ir3O(OAc)6(H2O)3][OAc], H2[IrCl6], the like, and mixtures thereof. In an embodiment, the iridium compounds may be selected from the group consisting of acetates, oxalates, acetoacetates, the like, and mixtures thereof. In an embodiment, the iridium compounds may be one or more acetates.

In an embodiment, the catalyst may be used with a co-catalyst. In an embodiment, co-catalysts may include metals and metal compounds selected from the group consisting of osmium, rhenium, ruthenium, cadmium, mercury, zinc, gallium, indium, and tungsten, their compounds, the like, and mixtures thereof. In an embodiment, co-catalysts may be selected from the group consisting of ruthenium compounds, osmium compounds, and mixtures thereof. In an embodiment, co-catalysts may be one or more ruthenium compounds. In an embodiment, the co-catalysts may be one or more acetates.

The reaction rate depends upon the concentration of the catalyst in the reaction mixture in reactor 210. In an embodiment, the catalyst concentration may be in a range from about 1.0 mmol to about 100 mmol catalyst per liter (mmol/l) of reaction mixture. In some embodiments the catalyst concentration is at least 2.0 mmol/l, or at least 5.0 mmol/l, or at least 7.5 mmol/l. In some embodiments the catalyst concentration is at most 75 mmol/l, or at most 50 mmol/l, or at least 25 mmol/l. In particular embodiments, the catalyst concentration is from about 2.0 to about 75 mmol/l, or from about 5.0 to about 50 mmol/l, or from about 7.5 to about 25 mmol/l.

In an embodiment, the carbonylation reaction in reactor 210 of system 200 may be performed in the presence of a catalyst stabilizer. Suitable catalyst stabilizers include those known to the industry. In general, there are two types of catalyst stabilizers. The first type of catalyst stabilizer may be a metal iodide salt such as LiI. The second type of catalyst stabilizer may be a non-salt stabilizer. In an embodiment, non-salt stabilizers may be pentavalent Group VA oxides. See U.S. Pat. No. 5,817,869, which is herein incorporated by reference. In an embodiment, catalyst stabilizer may be a phosphine oxide. In an embodiment, the catalyst stabilizer may be a triphenylphosphine oxide ("TPPO").

The amount of pentavalent Group VA oxide, when used, generally is such that a ratio to rhodium is greater than about 60:1. In an embodiment, the ratio of the pentavalent Group 15 oxide to rhodium is from about 60:1 to about 500:1. In some embodiments, from about 0.1 to about 3 M of the pentavalent Group 15 oxide may be in the reaction mixture, alternatively, from about 0.15 to about 1.5 M, alternatively, from 0.25 to 1.2 M, of the pentavalent Group 15 oxide may be in the reaction mixture.

In other embodiments, the reaction may occur in the absence of a stabilizer selected from the group of metal iodide salts and non-metal stabilizers such as pentavalent Group 15 oxides. In further embodiments, the catalyst stabilizer may consist of a complexing agent which is brought into contact with the reaction mixture stream 211 in the flash vessel 220.

In an embodiment, hydrogen may also be fed into the reactor 210. Addition of hydrogen can enhance the carbonylation efficiency. In an embodiment, the concentration of hydrogen may be in a range of from about 0.1 mol % to about 5 mol % of carbon monoxide in the reactor 210. In an embodiment, the concentration of hydrogen may be in a range of from about 0.3 mol % to about 3 mol % of carbon monoxide in the reactor 210.

In an embodiment, the carbonylation reaction in reactor 210 of system 200 may be performed in the presence of water. In an embodiment, the concentration of water is from about 2 wt % to about 14 wt % based on the total weight of the reaction mixture. In an embodiment, the water concentration is from about 2 wt % to about 10 wt %. In an embodiment, the water concentration is from about 4 wt % to about 8 wt %.

In an embodiment, the carbonylation reaction may be performed in the presence of methyl acetate. Methyl acetate may be formed in situ. In embodiments, methyl acetate may be added as a starting material to the reaction mixture. In an embodiment, the concentration of methyl acetate may be from about 2 wt % to about 20 wt % based on the total weight of the reaction mixture. In an embodiment, the concentration of methyl acetate may be from about 2 wt % to about 16 wt %. In an embodiment, the concentration of methyl acetate may be from about 2 wt % to about 8 wt %. Alternatively, methyl acetate or a mixture of methyl acetate and methanol from byproduct streams of the methanolysis of polyvinyl acetate or ethylene-vinyl acetate copolymers can be used for the carbonylation reaction.

In an embodiment, the carbonylation reaction may be performed in the presence of methyl iodide. Methyl iodide may be a catalyst promoter. In an embodiment, the concentration of methyl iodide may be from about 0.6 wt % to about 36 wt % based on the total, weight of the reaction mixture. In an embodiment, the concentration of methyl iodide may be from about 4 wt % to about 24 wt %. In an embodiment, the concentration of methyl iodide may be from about 6 wt % to about 20 wt %. Alternatively, methyl iodide may be generated in the reactor 210 by adding HI.

In an embodiment, methanol and carbon monoxide may be fed to the reactor 210 in stream 212 and stream 214, respectively. The methanol feed stream to the reactor 210 may come from a syngas-methanol facility or any other source. As seen in FIG. 1, methanol does not react directly with carbon monoxide to form acetic acid. It is converted to methyl iodide by the HI present in the reactor 210 and then reacts with carbon monoxide and water to give acetic acid and regenerate the HI.

In an embodiment, the carbonylation reaction in reactor 210 of system 200 may occur at a temperature within the range of about 120° C. to about 250° C., alternatively, about 150° C. to about 250° C., alternatively, about 150° C. to about 200° C. In an embodiment, the carbonylation reaction in reactor 210 of system 200 may be performed under a pressure within the range of about 200 psig (14 kg/cm$^2$) to 2000 psig (140 kg/cm$^2$), alternatively, about 200 psia (14 kg/cm$^2$) to about 1,000 psia (70 kg/cm$^2$), alternatively, about 300 psia (21 kg/cm$^2$) to about 500 psia (35 kg/cm$^2$).

In an embodiment, the reaction mixture may be withdrawn from the reactor 210 through stream 211 and is flashed in flash vessel 220 to form a vapor stream 226 and a liquid stream 221. The reaction mixture in stream 211 may comprise acetic acid, methanol, methyl acetate, methyl iodide, carbon monoxide, carbon dioxide, water, HI, heavy impurities, or combinations thereof. In one-particular embodiment, the stream 211 comprises acetic acid 70.30 wt %, methanol 0.04 wt % methyl acetate 0.91 wt %, methyl iodide 10.73 wt %, CO 0.13 wt %, CO2 0.09 wt %, water 14.39 wt %, HI 3.37 wt %, heavy imps 0.01 wt %, catalyst 0.03 wt %. The flash vessel 220 may generally comprise any configuration for separating vapor and liquid components via a reduction in pressure. For example, the flash vessel 220 may comprise a flash tank, nozzle, valve, or combinations thereof.

The flash vessel 220 may have a pressure below that of the reactor 210. In an embodiment, the flash vessel 220 may have a pressure of from about 10 psig to 100 psig. In an embodiment, the flash vessel 220 may have a temperature of from about 100° C. to 160° C.

The vapor stream 226 may comprise acetic acid and other volatile components such as methanol, methyl acetate, methyl iodide, carbon monoxide, carbon dioxide, water, entrained HI, complexed HI, heavy impurities, and mixtures thereof. The liquid stream 221 may comprise acetic acid, methanol, methyl acetate, methyl iodide, carbon monoxide, carbon dioxide, water, HI, heavy impurities, and mixtures thereof. In particular, it may comprise the catalyst, complexed HI, HI, an azeotrope of HI and water, and mixtures thereof. The liquid stream 221 may further comprise sufficient amounts of water and acetic acid to carry and stabilize the catalyst, non-volatile catalyst stabilizers, or combinations thereof. The liquid stream 221 may recycled to the reactor 210. The vapor stream 226 may be communicated to light-ends column 230 for distillation. In one particular embodiment, the stream 226 comprises acetic acid 49.77 wt %, methanol 0.04 wt %, methyl acetate 2.43 wt %, methyl iodide 33.03 wt %, CO 0.45 wt %, CO2 0.31 wt %, water 13.79 wt %, HI 0.11 wt %, heavy imps 0.03 wt %. In one particular embodiment, the stream 221 comprises liquid acetic acid 79.04 wt %, methyl iodide 1.53 wt %, water 14.67 wt %, HI 4.71 wt %, catalyst 0.05 wt %

In an embodiment, the vapor stream 226 may be distilled in a light-ends column 230 to form an overhead stream 232, a crude acetic acid product stream 236, and a bottom stream 231. In an embodiment, the light-ends column 230 may have at least 10 theoretical stages or 16 actual stages. In an alternative embodiment, the light-ends column 230 may have at least 14 theoretical stages. In an alternative embodiment, the light-ends column 230 may have at least 18 theoretical stages. In embodiments, one actual stage may equal approximately 0.6 theoretical stages. Actual stages can be trays or packing. The reaction mixture may be fed via stream 226 to the light-ends column 230 at the bottom or the first stage of the column 230.

Stream 232 may comprise HI, heavy impurities, water, carbon monoxide, carbon dioxide, methyl iodide, methyl acetate, methanol and acetic acid, a complexing agent (optionally), and mixtures thereof. Stream 231 may comprise acetic acid, methanol, methyl iodide, methyl acetate, carbon monoxide, carbon dioxide, HI, water, heavy impurities, and mixtures thereof. Stream 236 may comprise acetic acid, methanol, methyl iodide, methyl acetate, carbon monoxide, carbon dioxide, HI, water, heavy impurities, a complexing agent (optionally), and mixtures thereof. Streams 232, 231, and 236, as well as other streams discussed herein, may also comprise complexing agent at varying concentrations, depending on where the complexing agent is added to the system.

In an embodiment, the light-ends column 230 may be operated at an overhead pressure within the range of 20 psia (1.4 kg/cm2) to 40 psia (2.8 kg/cm2), alternatively, the overhead pressure may be within the range of 30 psia (2 kg/cm2) to 35 psia (2.5 kg/cm2). In an embodiment, the overhead temperature may be within the range of 95° C. to 135° C., alternatively, the overhead temperature may be within the range of 110° C. to 135° C., alternatively, the overhead temperature may be within the range of 125° C. to 135° C. In an embodiment, the light-ends column 230 may be operated at a bottom pressure within the range of 25 psia (1.8 kg/cm2) to 45 psia (3.2 kg/cm2), alternatively, the bottom pressure may be within the range of 30 psia (2.1 kg/cm2) to 40 psia (2.8 kg/cm2).

In an embodiment, the bottom temperature may be within the range of 115° C. to 155° C., alternatively, the bottom temperature is within the range of 125° C. to 135° C. In an embodiment, crude acetic acid in stream 236 may be emitted from the light-ends column 240 as a liquid sidedraw. Stream 236 may be operated at a pressure within the range of 25 psia (1.8 kg/cm2) to 45 psia (3.2 kg/cm2), alternatively, the pressure may be within the range of 30 psia (2.1 kg/cm2) to 40 psia (2.8 kg/cm2). In an embodiment, the temperature of stream 236 may be within the range of 110° C. to 140° C., alternatively, the temperature may be within the range of 125° C. to 135° C. Stream 236 may be taken between the fifth to the eighth actual stage of the light-ends column 230.

The overhead vapor in stream 232 from the light-ends column 230 may be condensed and separated in a decanter 234 to form a light, aqueous phase and a heavy, organic phase. The heavy, organic phase may be recycled to the reactor 210 in stream 238 via stream 212, for example. The stream 238 may comprise acetic acid, methanol, methyl acetate, methyl iodide, carbon monoxide, carbon dioxide, water, HI, heavy impurities, a complexing agent (optionally), and mixtures thereof.

The light, aqueous phase may be recycled to the light-ends column 230 in stream 235 or may be recycled to the reactor 210 in stream 239 via stream 212, for example. The stream 235 may comprise acetic acid, methanol, methyl acetate, methyl iodide, carbon monoxide, carbon dioxide, water, HI, heavy impurities, a complexing agent (optionally), and mixtures thereof. The heavy, organic phase in stream 238 may comprise methyl iodide, and methyl acetate, and mixtures thereof. The light, aqueous phase in streams 236 and 239 may comprise water (greater than 50%), acetic acid, comprise methanol, methyl acetate, methyl iodide, carbon monoxide, carbon dioxide, heavy impurities, a complexing agent (optionally), and mixtures thereof. Make-up water may be introduced into the decanter 234 via stream 233. Streams 239 and 238 may be considered to be in the light-ends area 204 and the recycle area 208.

In one or more embodiments, the crude acetic acid in stream 236 may be optionally subjected to further purification, e.g., drying-distillation, in drying column 240 to remove water and heavy-ends distillation of stream 241. Stream 241 may be fed to heavy-ends column 250 where heavy impurities such as propionic acid may be removed in stream 251 and final acetic acid product may be recovered in stream 256.

In an embodiment, a complexing agent may be continually introduced into the system 200 via stream 260. In FIG. 2, stream 260 mixes with the flash vessel 220 vapors to continually introduce the complexing agent to the components of the flash vessel 220 vapor stream 226. In an alternative embodiment, stream 260 may continually introduce the complexing agent into any equipment or streams in the reaction area 202, light-ends area 204, recycle area 208, or combinations thereof. For example, stream 260 may continually introduce the complexing agent into the flash vessel 220, light-ends column 230, reactor 210, streams 211, 212, 214, 221, 226, 231, 232, 233, 235, 236, 238, 239, or combinations thereof. Therefore, although stream 260 is shown in FIG. 2 as mixing with the vapor stream emitted from the flash vessel 220, it is contemplated that alternative embodiments may include stream 260 as mixing with any equipment or stream in the reaction area 202, light-ends area 204, recycle area 208, or combinations thereof.

In an embodiment, the complexing agent may be continually introduced in stream 260 as a solution. In an embodiment, the complexing agent may be continually introduced in stream 260 as a complexing agent solution comprising the complexing agent and a solvent. In an embodiment, the complexing agent solution may comprise an acetic acid solution. The nature of the solvent or diluent generally may not be critical so long as the solvent or diluent does not interfere with the carbonylation reaction or the purification of the acetic acid in the purification area 206.

Those skilled in the art of homogeneous processes having the benefit of this disclosure, and in particular those processes that require a flashing step to disengage involatile catalysts and additives, will appreciate that attrition rates of catalysts and additives solely related to entrainment will be a function of several variables. Among these variables are reactor size feed rate, and flasher size and flashing rate. They will also appreciate that a make-up solution of TPPO in acetic acid ("HOAc") could be as concentrated as the solubility limit of TPPO in HOAc allows, which is about 50 wt % or as dilute as a few PPM.

A primary consideration is that the flow rate and TPPO concentration of the make-up stream are matched such that the steady state concentration of TPPO in the reactor. This can normally vary from its high and low point between batch additions of up to 1.5 wt %, is now controlled within a target range of preferably +/−0.5 wt % and most preferably +/−0.2 wt %. Thus for example in a process with an attrition rate of 1 wt % per month from the reactor, a monthly batch addition could be replaced by a continually metered stream corresponding to an average daily TPPO addition of about 0.03 wt %"

In an embodiment, no solvent or diluent may be used. In an embodiment, the solvent or diluent is one or more of the liquid constituents of the reaction mixture in reactor 210, e.g., acetic acid, methanol, methyl iodide, water, or combinations thereof. In an embodiment, the solvent or dilution may be acetic acid, methanol, or both. Similarly, the amount of solvent or diluents used in this context is not critical and may be adjusted broadly depending on process economy. The use of a solvent or diluent may be advantageous to ensure fast and even distribution and contact of the complexing agent with HI.

In an embodiment, when the complexing agent is introduced to the system 200 separately and independently from the reaction mixture and from any recycle stream it may be advantageous to employ a solvent or diluent. Such a "recycle stream" may be a product or composition which is recovered from a processing step downstream of the flash vessel and which is recycled to the reactor, flash vessel, or light-ends column. In an alternative embodiment, when the complexing agent is brought into contact with the reaction mixture in the flash vessel 220, for example, by adding it to stream 231 prior to introducing the stream 231 to the flash vessel 220, the complexing agent may be introduced in substance, i.e., in undiluted form, as the liquid constituents of the stream 231 act as solvents or diluents.

In an embodiment, the complexing agent may comprise a catalyst stabilizer. In an embodiment, the complexing agent may comprise a phosphine oxide. In an embodiment, the complexing agent may comprise a triphenylphosphine oxide.

Without intending to be limited by theory, it is believed TPPO may interact with HI to form a complex, as is discussed in the examples below. A HI complex may reduce a concentration of HI in the purification area 206 for at least the following reasons: i) the complexing agent, e.g., TPPO, may have a relatively high boiling point and therefore may be retained in the liquid stream 221 of the flash vessel 220 where it may inhibit or at least significantly reduce the tendency of HI to be entrained in the vapor stream 226; ii) the complexing agent may, by forming a complex with HI, act as a scavenger of HI and reducing the amount of HI which may become entrained in the vapor stream 226 and subsequently passed to the light-ends area 204; and iii) even if an amount of a HI complex becomes entrained in the vapor stream 226 and passes to the light-ends area 204, the HI complex (which may have a relatively high boiling point) may be recovered in the bottom stream 231 of the light-ends column 230. Thus, forming an HI complex enables the system 200 to inhibit or at least reduce transport of HI into the purification area 206 by enhancing recovery of HI (as a HI complex) in the reaction area 202 (e.g., in the liquid stream 221 of the flash vessel 220) and in the light-ends area 204 (e.g., in the bottom stream 231 of the light-ends column 230).

Recovery of HI (as a HI complex) also may counter effects of HI volatilization in the case of azeotropic breakdown. Hydrogen iodide forms a high boiling azeotrope in acetic acid solutions having greater than about 5 wt % water. If the water concentration (e.g., in the stream 231) falls below about 5 wt %, azeotropic breakdown and HI volatilization may occur. Such volatilization may lead to less HI in the bottom stream 231 obtained in the light-ends column 230 and returned to the reactor 210, and thus, may adversely impact reactor iodide inventory.

Additionally, in the case of azeotropic breakdown, volatilized HI may become part of the stream 236 which is withdrawn from the light-ends column 230 for purification in the purification area 206. Because the complexing agent (e.g., TPPO) forms a complex with HI, continually introducing a complexing agent may act as a scavenger for the volatized HI in the event of azeotropic breakdown in the light-ends column 230 and may inhibit or at least reduce transfer of volatized HI into the purification area 206. Because some complexing agents (e.g., TPPO) double as a catalyst stabilizer for carbonylation reactions in reactor 210, the reaction in reactor 210 experiences little detriment as a result of any HI complex recycled to reactor 210.

Figure 3:
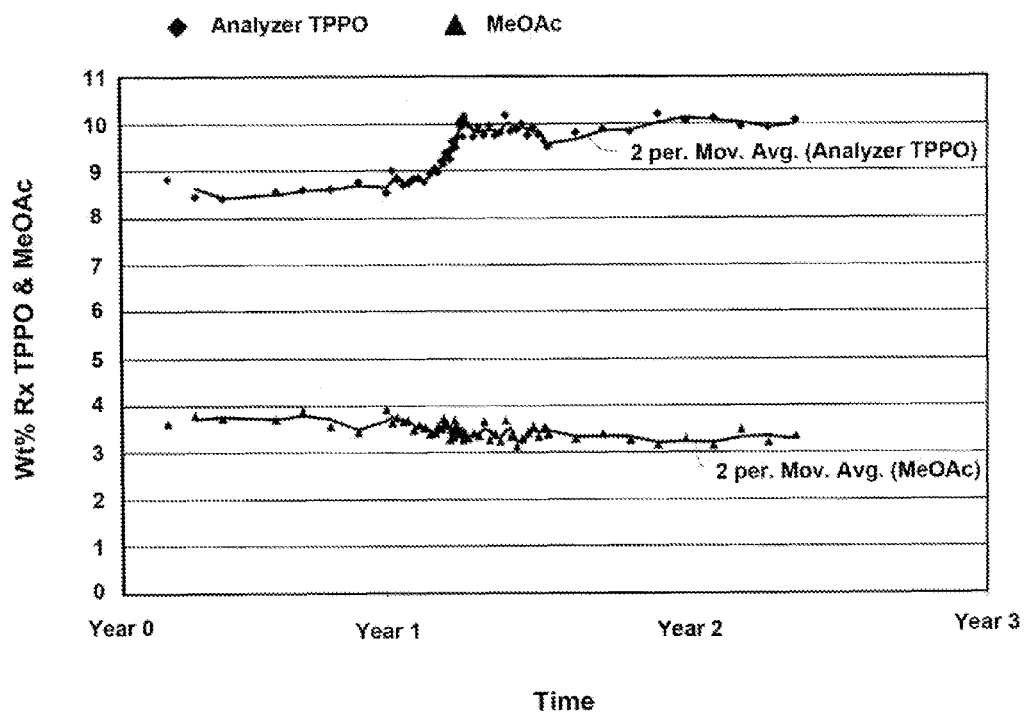
FIG. 3 illustrates a graph of concentrations of a complexing agent and methyl acetate over time after batch addition of the complexing agent.

FIG. 3 illustrates a graph of concentrations of a complexing agent (TPPO) and methyl acetate (MeOAc) over time after batch addition of the complexing agent. The concentrations are shown as a weight % of a reaction mixture in a carbonylation reactor, like reactor 210. Concentrations were obtained using an online infrared analyzer. The time period for data shown in FIG. 3 was approximately fifty-two hours.

The data shown in FIG. 3 for reactor TPPO and MeOAc concentrations are associated with a continuous methanol carbonylation unit equipped with a reactor, reactor on-line infrared analyzer, flash tank, light ends column, decanter and drying column. During the 52 hour period illustrated in FIG. 3, the process was in steady state operation at constant feed rate, constant temperature and steady state catalyst concentration. Those skilled in the art of rhodium catalyzed methanol carbonylation having the benefit of this disclosure will appreciate that under these steady state conditions, MeOAc concentration is also expected to be in steady state.

Over the fifty-two hour period shown in the graph of FIG. 3, after batch addition of TPPO to the reactor, TPPO concentration increased from about 8.5 wt % to about 10 wt %, and MeOAc concentration decreased from about 3.8 wt % to about 3.5 wt %. The drop in MeOAc concentration suggests an increase in activity resulting from an increase in Rh(I)/Rh (II) ratio due to the increase in concentration of TPPO. Thus, FIG. 3 demonstrates the magnitude for fluctuations in concentrations of TPPO and methyl acetate with batch additions of TPPO.

In rhodium catalyzed methanol carbonylation, HI has plays two roles. It's positive role is associated with the fact that it is a necessary intermediate in shuttling "methyl" groups from feed MeOAc (which is incapable of undergoing direct catalysis to HOAc) to MeI. Without the ability to continuously regenerate MeI, reaction would shut down. The negative role of HI is associated with the fact that it oxidatively adds to the active Rh species, Rh (I), to form an inactive (for MeOH carbonylation) Rh (III) species, leading to various byproducts. Thus, some of the active Rh is diverted from its desired task of catalyzing HOAc formation to undesired side reactions.

Reactor feed can be pure MeOH, pure MeOAc or a mixture thereof, but for all intents and purposes it can be considered to be a pure feed of MeOAc, as MeOH is instantly esterified to MeOAc upon contacting the reactor. The steady state concentration of MeOAc in the reactor is a function of Rh (I) concentration and MeI concentration as these are the two principal components that control rate. If there is insufficient concentration of either or both of these components, then unreacted feed (MeOAc) will build up in the reactor. Acetic producers closely watch reactor MeOAc concentration as, similar to HI, it has dual character. Higher steady state MeOAc concentrations imply that existing Rh and/or MeI concentrations are working hard to keep up in converting feed to HOAc.

This has a positive impact and a negative impact. On the good side, if all of the catalyst is being employed in MeOH carbonylation, then there is no idle catalyst sitting round to get involved in alternate byproduct catalytic pathways by reacting with HI to form various Rh (III) species. Generally speaking, MeOH carbonylation processes that run at higher steady state reactor MeOAc concentration have lower rates of byproduct formation than those processes running at lower reactor MeOAc concentration. On the bad side, if reactor MeOAc gets too high, it can lead to downstream upsets with subsequent reactor shutdown. Each acetic producer has its own target concentration for reactor MeOAc and strives to maintain this concentration within certain controlled limits.

TPPO interacts sufficiently strongly with HI to limit its ability to oxidatively add to Rh (I) and form inactive Rh (III) species. Therefore, at constant reactor MeOAc feed rate, as TPPO concentration in reactor increases, the ratio of Rh (I)/Rh (III) increases and steady state MeOAc concentration will decrease.

TPPO is a thermally and chemical stable additive and is essentially involatile. Thus, under normal circumstances, once added to the reactor, its concentration should be invariant as TPPO in the HOAc stream entering the flash tank should be quantitatively returned to the reactor in flash tank bottom recycle. However, there is unavoidable entrainment of TPPO in flash tank overhead and thus through slow attrition, target reactor TPPO concentration or concentration range cannot be maintained without occasional additions. By metering TPPO on a continuous basis to flash tank or light ends column, the benefit is derived of not only lower iodide concentration in the purification section, but also more rigorously controlled HI and therefore Rh (I) and therefore MeOAc concentration in the reactor.

Additional information on this behavior can be found in Jane. H. Jones, "The CATIVA Process for the Manufacture of Acetic Acid", 44 (3) *Platinum Metals Rev.* 94-105 (2000); Jones, Roberts and Taylor, "C1 to Acetyls: Catalysis and Process", 18 *Catalysis Today* 325-354 (1993); and Noel Hallinan & James Hinnenkamp, "Rhodium Catalyzed Methanol Carbonylation: New Low Water Technology", *Catalysis of Organic Reactions*, pp. 545-556 (Michael E. Ford ed. 2000).

Without intending to be limited by theory, it is believed that continually introducing the complexing agent (e.g., TPPO) into the process at different points in the reaction area 202 or light-ends area 204 of system 200 reduces the likelihood of HI transfer to the purification area 206.

TPPO functions as a catalyst stabilizer, which is related to its ability to complex with HI. Complexation with HI minimizes oxidative addition of HI to Rh (I) to form Rh (I) species. The latter species are inactive for MeOH carbonylation in reactor and are more prone to precipitation in the flash tank. Without intending to be limited by theory, continuous introduction of TPPO into the process at different points in the reaction area 202 or light-ends area 204 of system 200 may stabilize levels (i.e. concentrations) of TPPO and HI in the acetic acid production process and system 200.

As may be deduced from FIG. 3, batch additions of TPPO in reactor 210 lead to large fluctuations in TPPO and HI concentrations over time, where HI concentration increases as TPPO concentration decreases due to loss. By continually introducing TPPO, an amount of HI concentration fluctuation is reduced because an amount of TPPO concentration fluctuation is at least reduced if not significantly reduced. Thus, an unintended benefit of using TPPO as a complexing agent may be a dampened need for batch additions of TPPO as a catalyst stabilizer.

In an embodiment, continually introducing TPPO may comprise continually metering TPPO in solution (e.g., an acetic acid solution) using a gas or liquid metering technology known in the art such as turbine meters, coriolis meters, ultrasonic meters, PD meters, or combinations thereof. Continuously metering may comprise uniformly injecting a known concentration of TPPO in solution (e.g., an acetic acid solution).

The reaction of the complexing agent with HI is rapid and is generally quantitative at a temperature of about 20° C. In embodiments, the reaction takes place when the complexing agent is brought into contact with a process stream which is upstream of the heavy-ends distillation column.

In an embodiment, the reaction mixture in reactor 210 does not comprise complexing agent (e.g., TPPO) other than the complexing agent continually introduced into the system 200 and which has been recycled to the reactor 210.

In an embodiment, the amount of complexing agent which is brought into contact with the HI is generally not critical so long as the complexing agent is provided in an effective amount. An effective amount in this context is the amount of complexing agent which is capable of scavenging at least a part of the HI which is present at a point in the system 200. The amount of complexing agent that is added is governed by the attrition rate of the complexing agent from reactor rather than the HI concentration.

In an embodiment, the rate at which complexing agent is introduced into the system 200 may be adjusted depending on the HI content. In some embodiments, the complexing agent may be introduced in an amount of at least about 0.1 mol per mol HI. In alternative embodiments, at least about 0.5 mol complexing agent, or at least about 1 mol complexing agent, or at least about 1.5 mol complexing agent, per mol HI is introduced. In alternative embodiments, the complexing agent may be introduced in an amount of from about 0.1 to about 10 mol per mol HI. In alternative embodiments, the amount of complexing agent is from about 0.25 to about 7.5 mol, or from about 0.5 to about 5 mol, or from about 0.75 to about 2.5 mol, per mol HI.

In further alternative embodiments, the amount of complexing agent is from about 1 to about 10 mol, or from about 1 to about 7.5 mol, or from about 1 to about 5 mol, per mol HI. In alternative embodiments, the complexing agent may be introduced in an amount from about 0.1 to about 1.5 mol per mol HI. In alternative embodiments, the amount of complexing agent introduced may be from about 0.1 to about 1.3 mol, or from about 0.1 to about 1.1 mol, per mol HI. In further alternative embodiments, the amount of complexing agent is from about 0.5 to about 3 mol, or from about 0.5 to about 2 mol, or from about 0.5 to about 1.5 mol, per mol HI.

Generally, it is not detrimental to the subsequent separation and purification of the final acetic acid product if the molar amount of complexing agent exceeds the molar amount needed to complex HI, so long as the boiling point of the complexing agent is sufficiently higher than the boiling point of the vapor stream 226 which emits from the flash vessel 220 and/or the stream 236 which emits from the light-ends column 230. For example, the boiling point of the complexing agent is sufficiently higher when the boiling point is at least 15° C., alternatively, at least 30° C., or alternatively, at least 50° C. above the boiling point of the crude acetic acid in stream 236.

In particular variants of these embodiments, the complexing agent may be introduced in the flash vessel 220 in an amount from about 0.1 to about 1.5 mol per mol HI. In alternative variants, the amount of complexing agent is from about 0.1 to about 1.3 mol, or from about 0.1 to about 1.1 mol, per mol HI. In further alternative embodiments, the amount of complexing agent is from about 0.5 to about 3 mol, or from about 0.5 to about 2 mol, or from about 0.5 to about 1.5 mol, per mol HI.

In further embodiments, the complexing agent may be introduced in the flash vessel 220 in an amount sufficient to establish a concentration of no more than about 20 wt % of the complexing agent in the liquid stream 221. In alternative embodiments, the complexing agent may be introduced to establish a concentration of no more than about 15 wt %, or no more than about 12 wt %, or no more than about 10 wt %, of the complexing agent in the liquid stream 221. In other embodiments, the complexing agent may be introduced in an amount sufficient to establish a concentration of at least about 0.5 wt % of the complexing agent in the liquid stream 221. In alternative embodiments, the complexing agent may be introduced in an amount sufficient to establish a concentration of at least about 1 wt %, or at least about 2.5 wt %, or at least about 4 wt %, of the complexing agent in the liquid stream 221. In particular embodiments, the complexing agent may be introduced in an amount sufficient to establish a concentration of from about 0.5 wt % to about 20 wt % of the complexing agent in the liquid stream 221.

In alternative embodiments, the complexing agent may be introduced in an amount sufficient to establish a concentration of from about 1 wt % to about 20 wt %, or from about 2.5 wt % to about 20 wt %, or from about 4 wt % to about 20 wt %, of the complexing agent in the liquid stream 221. In alternative embodiments, the complexing agent may be introduced in an amount sufficient to establish a concentration of from about 0.5 wt % to about 15 wt %, or from about 1 wt % to about 15 wt %, or from about 2.5 wt % to about 15 wt %, or from about 4 wt % to about 15 wt %, of the complexing agent in the liquid stream 221. In alternative embodiments, the complexing agent may be introduced in an amount sufficient to establish a concentration of from about 0.5 wt % to about 12 wt %, or from about 1 wt % to about 12 wt %, or from about 2.5 wt % to about 12 wt %, or from about 4 wt % to about 12 wt %, of the complexing agent in the liquid stream 221.

The liquid stream 221 can be recycled to the reactor 210. The recycled liquid stream 221 may introduce the complexing agent into the reactor 210, and consequently into the reaction mixture in reactor 210.

In certain embodiments, the amount of the complexing agent which is introduced in the flash vessel 220 may be adjusted to establish a steady state concentration of no more than about 20 wt % of the complexing agent in the reaction mixture. In alternative embodiments, the complexing agent may be introduced in the flash vessel 220 in an amount sufficient to establish a steady state concentration of no more than about 17 wt %, or no more than about 15 wt %, or no more than about 12 wt %, of the complexing agent in the reaction mixture. In other embodiments, the complexing agent may be introduced in the flash vessel 220 in an amount sufficient to establish a steady state concentration of at least about 2 wt % of the complexing agent in the reaction mixture. In alternative embodiments, the complexing agent may be introduced in the flash vessel 229 in an amount sufficient to establish a steady state concentration of at least about 5 wt %, or at least about 7 wt %, of the complexing agent in the reaction mixture.

In particular embodiments, the complexing agent may be introduced in the flash vessel 220 in an amount sufficient to establish a steady state concentration from about 2 wt % to about 20 wt % of the complexing agent in the reaction mixture. In alternative embodiments, the complexing agent may be introduced in the flash vessel 220 in an amount sufficient to establish a steady state concentration of from about 5 wt % to about 20 wt %, or from about 7 wt % to about 20 wt %, of the complexing agent in the reaction mixture. In alternative embodiments, the complexing agent may be introduced in the flash vessel 220 in an amount sufficient to establish a steady state concentration of from about 2 wt % to about 17 wt %, or from about 5 wt % to about 17 wt %, or from about 7 wt % to about 17 wt %, of the complexing agent in the reaction mixture.

In alternative embodiments, the complexing agent may be introduced in the flash vessel 220 in an amount sufficient to establish a steady state concentration of from about 2 wt % to about 15 wt %, or from about 5 wt % to about 15 wt %, or from about 7 wt % to about 15 wt %, of the complexing agent in the reaction mixture. In alternative embodiments, the complexing agent may be introduced in the flash vessel 220 in an amount sufficient to establish a steady state concentration of from about 2 wt % to about 12 wt %, or from about 5 wt % to about 12 wt %, or from about 7 wt % to about 12 wt %, of the complexing agent in the reaction mixture.

In general, the complexing agent may be introduced into the system 200 only continually. The process in accordance with the present disclosure differs from the prior an procedures at least in that complexing agent may be introduced into the system 200 downstream of reactor 210 and upstream of the purification area 206.

Despite efficient complexation, residual HI which may reach the light-ends column 230 may be easily separated from as a bottom product stream 231 of the light-ends area 204. Also, due to the removal of HI from the product stream in the earliest stage of the acetic acid work-up, side reactions which are caused by HI, i.e., the formation of undesirable long chain alkyl iodide contaminants in the product stream downstream from the flash vessel, are significantly reduced. Additionally, the reduced amounts of HI in the product streams downstream from the flash vessel 220 alleviate corrosion and engineering problems. Also, the complexing agent acts as a catalyst stabilizer. Therefore, problems caused by losses of catalyst due to deactivation or deposition are reduced or may even be avoided.

The beneficial effect of the complexing agent on the vaporization of HI is not restricted to the point of introduction into the system 200. Rather, as the complexing agent circulates in the system 200 by recycling the liquid stream 221 from the flash vessel 220 to the reactor 210, its presence in the reaction mixture aids in reducing the tendency of HI to vaporize in the flash vessel 220, thus aiding in reducing the amount of HI which may become entrained in the vapor stream 226. Therefore, upon continuous operation of the process, the amount of complexing agent which is brought into contact with the reaction mixture in the flash vessel 220 normally may be decreased as steady state conditions are achieved. Under steady state conditions, the amount of complexing agent which is brought into contact with the reaction mixture in the flash vessel 220 normally can be reduced to amounts necessary to maintain the desired steady state concentration of the complexing agent.

EXAMPLES

The following investigations and examples are intended to be illustrative only, and are not intended to be, nor should they be construed as, limiting the scope of the claimed subject matter in any way. The examples were performed using apparatus of FIG. 4 or FIG. 5. The examples show TPPO causes a low volatility for HI. It is believed this reduction in volatility is a result of formation of a HI complex.

Figure 4:
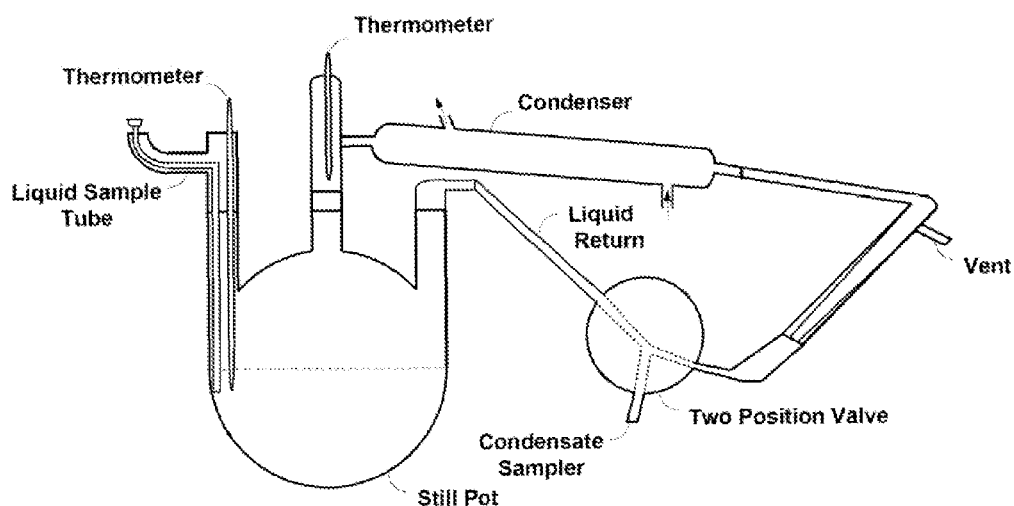
FIGS. 4 and 5 illustrate two recirculation apparatus for investigating the vapor liquid equilibrium ("VLE").

FIG. 4 illustrates a diagrammatic first recirculation apparatus (Apparatus 1) for investigating the VLE. The apparatus comprises a 3-neck round-bottomed flask ("Still Pot"). The first neck is equipped with a tube ("Liquid Sample Tube") for adding components to the liquid, or withdrawing samples from the liquid contained in the flask, and a thermometer measuring the temperature of the liquid contained in the flask. The second neck is equipped with a reflux/distillation head, and with a thermometer measuring the temperature of the vapor phase. The vapor is condensed in a condenser, and the condensate is conveyed back to the flask via a liquid return ("Liquid Return") to the third neck of the flask. The liquid return is equipped with a vent ("Vent") and a two position valve ("Two Position Valve") for withdrawing samples of the condensate.

Figure 5:
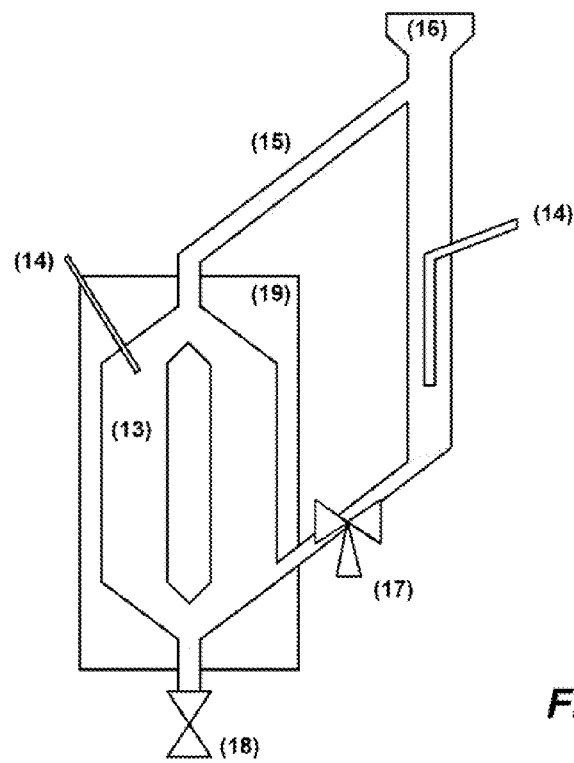

FIG. 5 illustrates a diagrammatic second recirculation apparatus (Apparatus 2) for investigating the VLE. The apparatus comprises a dual chambered circulation volume 13 as the still. The still is equipped with a recirculation line 15 which, in turn, connects to a condenser 16 and comprises a two position valve 17 for sampling the condensate. Additionally, the still is equipped with a bottom tap 18 for sampling the liquid. The still is enclosed by heating and insulating means 19. Both, the still 13 and the recirculation line 15 are provided with thermo-wells with thermocouples 14 connected to a temperature control unit (not shown).

Figure 6:
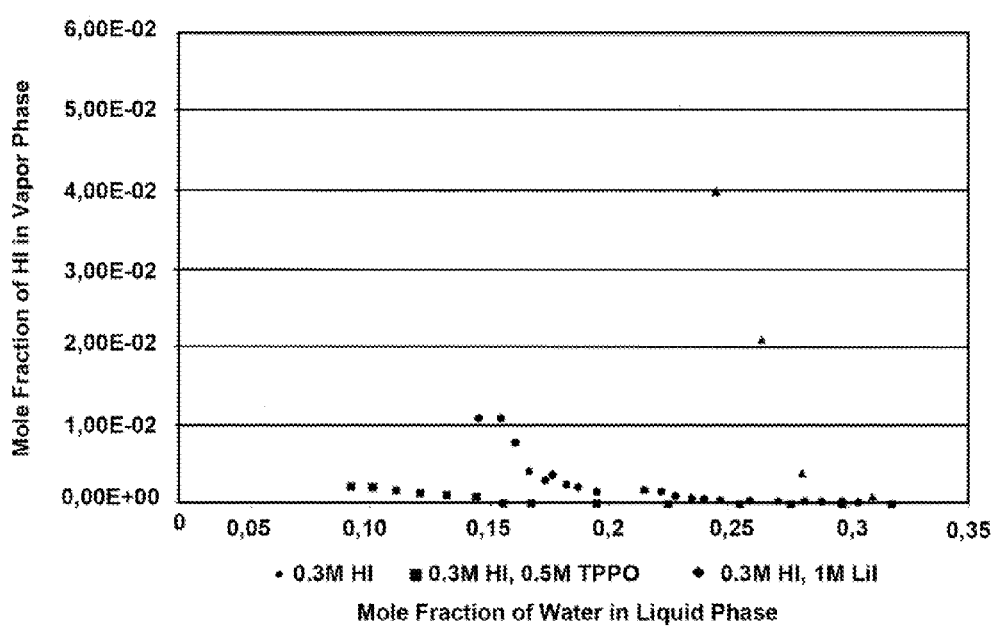
FIG. 6 depicts the results of investigations into the impact of triphenylphosphine oxide ("TPPO") and lithium iodide ("LiI") on the VLE of HI in aqueous acetic acid.

FIG. 6 shows that the presence of 1M LiI increases the volatility of HI whereas 0.5M TPPO reduces the volatility of HI.

Figure 7:
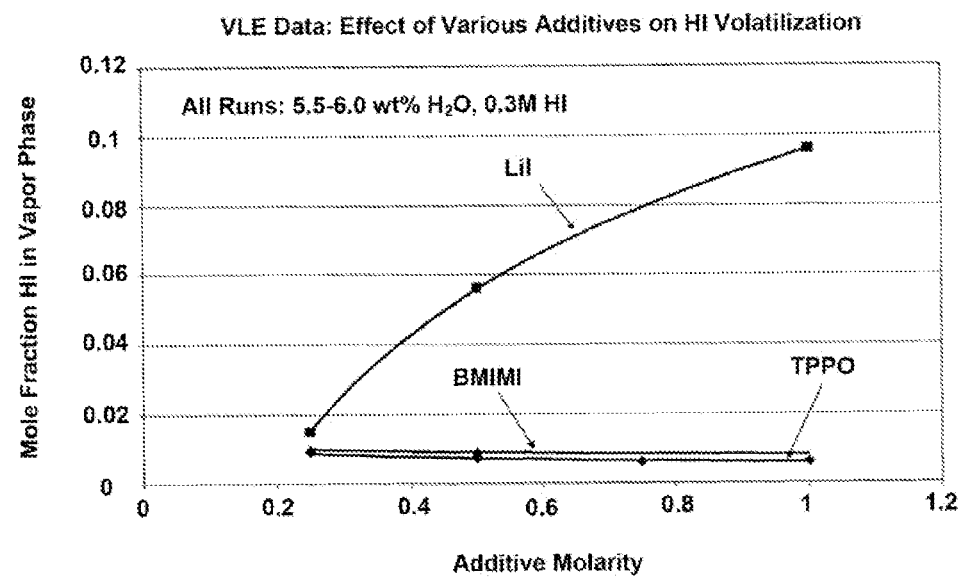
FIG. 7 depicts the results of investigations into the impact of TPPO, LiI, and 1-butyl, 3-methylimidazolium iodide ("BMIMI") on the VLE of HI in acetic acid comprising 5:5-6 wt % of water.
Figure 8:
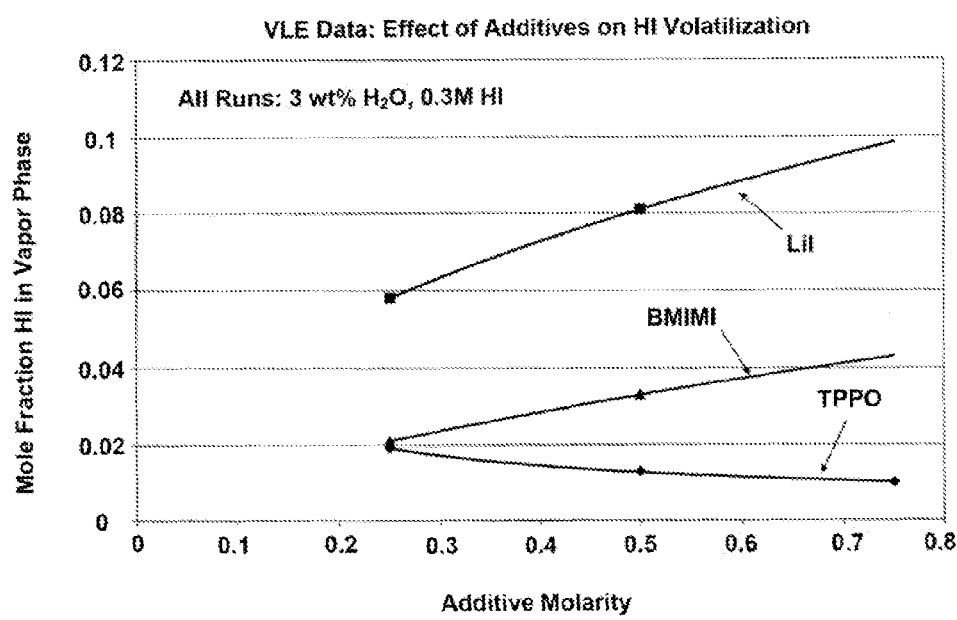
FIG. 8 depicts the results of investigations into the impact of TPPO, LiI, and BMIMI on the VLE of HI in acetic acid comprising 3 wt % of water.

FIGS. 7 and 8 show the effect of LiI, TPPO, and 1-butyl, 4-methylimidazolium iodide ("BMIMI") on the volatility of HI at a water concentration of 5.5-6 wt % and 3 wt %, respectively.

The following investigations and examples are intended to be illustrative only, and are not intended to be, nor should they be construed as, limiting the scope of the claimed subject matter in any way.

VLE Investigations

The investigations were carried out in two different types of recirculation apparatus as shown schematically in FIGS. 4 and 5. Apparatus 1 was used for the experiments described in Examples 1 to 3, the results of which are depicted in FIG. 6. Apparatus 2 was used for the experiments described in Examples 4 to 21 the results of which are compiled in Tables 2 and 3 and depicted in FIGS. 7 and 8.

General Procedure A:

In the case of Apparatus 1, a 1 l flask was charged with a total of 500 grams of appropriate amounts of acetic acid, water, HI and optionally TPPO or LiI. The stirred solution was brought to reflux. After one hour of condensation/liquid return, a 10-20 gram sample of vapor condensate was collected. A 0.2 ml sample was also removed from the flask for analysis. A volume of acetic acid equivalent to the volume of the removed condensate sample was added to the flask and the solution was allowed to reflux for about 30 minutes before the sampling procedure was repeated and a further aliquot of acetic acid was added. This procedure was repeated until the concentration of water in the flask had decreased to the desired level.

General Procedure B:

In the case of Apparatus 2, the 150 grams of a mixture of appropriate amounts of acetic acid, water, HI, LiI, TPPO, BMIMI, 1-butyl, 2,3-dimethylimidazolium iodide ("BDMIMI"), and 1-dodecyl, 3-methylimidazolium iodide ("DO- MIMI") were charged to the flask under atmospheric pressure and slight $N_2$ purge. The mixture was refluxed for about 1 hour during which period the condensate was recirculated to the flask. Thereafter, a sample of the condensate and a sample of the mixture were withdrawn for analysis, and the experiment was terminated.

Water concentration in condensed vapor samples and in pot liquid samples was measured by Karl Fischer titration. Iodide concentration in those experiments containing iodide was determined either by titration with silver nitrate or by a visible spectro-photometric method in which iodide is first rapidly oxidized to iodine by hydrogen peroxide and then quantified by the iodine absorption band at 475 nm.

Validation of VLE Apparatus 1 and VLE Apparatus 2:

As those skilled in the art having the benefit of this disclosure will appreciate, it is critical that the apparatus operate in adiabatic fashion in which only one equilibrium stage is present and in which there is no enrichment of the vapor in the more volatile component by partial condensation. As such, the suitability of Apparatus 1 and Apparatus 2 was validated before use by determining the water concentration in the vapor condensate at flask water concentrations of 5, 10 and 20 wt % in acetic acid. The extent of enrichment of the more volatile water in the vapor phase upon heating the samples to reflux and upon analyzing a condensed vapor sample and a liquid pot sample, matched well with previous literature values as shown in Table 1 where all values are expressed as mole fractions.

TABLE 1

Validation of VLE Apparatus 1 and VLE Apparatus 2 By Comparison with Prior Art Data

| $H_2O$, Liq | $H_2O^1$, Vap | $H_2O^2$, Vap | $H_2O^3$, Vap | $H_2O^4$, Vap |
|---|---|---|---|---|
| 0.15 | 0.26 | 0.23 | 0.26 | 0.23 |
| 0.28 | 0.41 | 0.41 | 0.41 | 0.4 |
| 0.47 | 0.61 | 0.6 | 0.61 | |

[1] = Apparatus 1
[2] = Apparatus 2
[3] = EP 0 506 240
[4] = Brown et al., Aust. J. Sci. Res. Series A 3, 306 (1950)

Example 1

General Procedure A 500 grams of a solution composed of 12 wt % water, 3.8 wt % HI and 84.2 wt % acetic acid was charged to the Apparatus 1 flask. As described above, the water concentration in the flask was decreased from 12 wt % to about 5 wt % in increments of about 0.5 wt % by removal of aliquots of condensed vapor sample and replenishing the flask with a similar volume of acetic acid. The water and iodide concentration of the condensed vapor sample and of the pot solution were determined after each removal, thus allowing the mole fractions of all components to be calculated. The results are depicted in FIG. 6 which shows a rapid increase in HI in the vapor phase as water concentration in the pot is lowered.

Example 2

500 grams of a solution composed of 12 wt % water, 3.8 wt % HI, 13.0 wt % TPPO and 71.2 wt % acetic acid was charged to Apparatus 1 and an experiment conducted as described in Example 1. The results are depicted in FIG. 6 which shows that in the presence of triphenylphosphine oxide, there is very little HI in the vapor phase compared to Example 1.

Example 3

500 grams of a solution composed of 12 wt % water, 3.8 wt % HI, 13.0 wt % LiI and 71.2 wt % acetic acid was charged to Apparatus 1 and an experiment conducted as described in Example 1. The results are depicted in FIG. 6 which shows that in the presence of LiI, there is a rapid increase in HI in the vapor phase, even when there remains a high mole fraction of water in the liquid phase.

Example 4

General Procedure B 150 grams of a solution composed of 5.8 wt % water, 3.7 wt % HI and 90.5 wt % acetic acid was charged to the Apparatus 2 flask. After one hour of refluxing, a condensed vapor sample and a pot sample were removed for analysis. The results are compiled in Table 2.

Example 5

Example 4 was repeated with an initial solution composed of 5.8 wt % water, 3.7 wt % HI, 6.7 wt % BMIMI and 83.8 wt % acetic acid. The results are compiled in Table 2 and depicted in FIG. 7.

Example 6

Example 4 was repeated with an initial solution composed of 5.8 wt % water, 3.7 wt % HI, 13.3 wt % BMIMI and 77.2 wt % acetic acid. The results are compiled in Table 2 and depicted in FIG. 7.

Example 7

Example 4 was repeated with an initial solution composed of 6.0 wt % water, 3.7 wt % HI, 6.7 wt % TPPO and 83.6 wt % acetic acid. The results are compiled in Table 2 and depicted in FIG. 7.

Example 8

Example 4 was repeated with an initial solution composed of 6.0 wt % water, 3.7 wt % HI, 13.3 wt % TPPO and 77.0 wt % acetic acid. The results are compiled in Table 2 and depicted in FIG. 7.

Example 9

Example 4 was repeated with an initial solution composed of 6.0 wt % water, 3.9 wt % HI, 3.3 wt % LiI and 86.8 wt % acetic acid. The results are compiled in Table 2 and depicted in FIG. 7.

Example 10

Example 4 was repeated with an initial solution composed of 5.5 wt % water, 3.8 wt % HI, 6.6 wt % LiI and 84.1 wt % acetic acid. The results are compiled in Table 2 and depicted in FIG. 7.

TABLE 2

Effect of LiI, TPPO, and BMIMI on Volatilization of
HI from Acetic Acid Containing 5.5-6 Wt % of Water

| Ex. | Additive | Additive Concentration [M] | Mol Fraction of HI in Condensed Vapor |
|---|---|---|---|
| 04 | None (control) | –/– | 0.012 |
| 05 | BMIMI | 0.25 | 0.01 |
| 06 | | 0.5 | 0.009 |
| 07 | TPPO | 0.25 | 0.009 |
| 08 | | 0.5 | 0.007 |
| 09 | LiI | 0.25 | 0.015 |
| 10 | | 0.5 | 0.058 |

Example 11

Example 4 was repeated with an initial solution composed of 2.9 wt % water, 3.7 wt % HI and 93.4 wt % acetic acid. The results are compiled in Table 3.

Example 12

Example 4 was repeated with an initial solution composed of 2.9 wt % water, 3.7 wt % HI, 6.7 wt % BMIMI and 86.7 wt % acetic acid. The results are compiled in Table 3 and depicted in FIG. 8.

Example 13

Example 4 was repeated with an initial solution composed of 2.9 wt % water, 3.7 wt % HI, 13.3 wt % BMIMI and 80.1 wt % acetic acid. The results are compiled in Table 3 and depicted in FIG. 8.

Example 14

Example 4 was repeated with an initial solution composed of 2.9 wt % water, 3.7 wt % HI, 7.0 wt % BDMIMI and 86.4 wt % acetic acid. The results are compiled in Table 3 and depicted in FIG. 8.

Example 15

Example 4 was repeated with an initial solution composed of 2.9 wt % water, 3.7 wt % HI, 9.5 wt % DOMIMI and 83.9 wt % acetic acid. The results are compiled in Table 3.

Example 16

Example 4 was repeated with an initial solution composed of 2.9 wt % water, 3.7 wt % HI, 6.7 wt % triphenylphosphine oxide, 6.7 wt % BMIMI and 80.0 wt % acetic acid. The results are compiled in Table 3 and depicted in FIG. 8.

Example 17

Example 4 was repeated with an initial solution composed of 2.9 wt % water, 3.7 wt % HI, 6.7 wt % BMIMI, 3.3 wt % LiI and 83.4 wt % acetic acid. The results are compiled in Table 3 and depicted in FIG. 8.

Example 18

Example 4 was repeated with an initial solution composed of 3.1 wt % water, 3.9 wt % H, 6.6 wt % TPPO and 86.4 wt % acetic acid. The results are compiled in Table 3 and depicted in FIG. 8.

Example 19

Example 4 was repeated with an initial solution composed of 2.9 wt % water, 3.7 wt % HI, 13.3 wt % TPPO and 80.1 wt % acetic acid. The results are compiled in Table 3 and depicted in FIG. 8.

Example 20

Example 4 was repeated with an initial solution composed of 2.9 wt % water, 3.7 wt % HI, 3.3 wt % LiI and 90.1 wt % acetic acid. The results are compiled in Table 3 and depicted in FIG. 8.

Example 21

Example 4 was repeated with an initial solution composed of 2.9 wt % water, 3.7 wt. % HI, 6.6 wt % LiI and 86.8 wt % acetic acid. The results are compiled in Table 3 and depicted in FIG. 8.

TABLE 3

Effect of LiI, TPPO, BMIMI, BDMIMI, and DOMIMI on Volatilization
of HI From Acetic Acid Containing 3 wt % of Water

| Ex. | Additive | Additive Concentration [M] | Mol Fraction of HI in Condensed Vapor |
|---|---|---|---|
| 11 | None (control) | –/– | 0.048 |
| 12 | BMIMI | 0.25 | 0.021 |
| 13 | | 0.5 | 0.033 |
| 14 | BDMIMI | 0.25 | 0.023 |
| 15 | DOMIMI | 0.25 | 0.041 |
| 16 | TPPO + BMIMI | 0.25 + 0.25 | 0.017 |
| 17 | LiI + BMIMI | 0.25 + 0.25 | 0.049 |
| 18 | TPPO | 0.25 | 0.019 |
| 19 | | 0.5 | 0.013 |
| 20 | LiI | 0.25 | 0.058 |
| 21 | | 0.5 | 0.081 |

In particular, Table 2 and FIG. 6 illustrate that the effect of the complexing agent (BMIMI) on the suppression of HI is similar to that of TPPO. In contrast, LiI increases the volatility of HI in a concentration dependent manner, i.e., an increase of almost an order of magnitude is observed when the concentration of LiI is increased from 0.25 M to 1.0 M.

INCORPORATED REFERENCES

The following patents are hereby incorporated by reference in their entirety and for all purposes as if expressly set forth verbatim herein:

U.S. Pat. No. 6,552,221, entitled, "Process Control for Acetic Acid Manufacture", and issued Apr. 22, 2003, to Millennium Petrochemicals, Inc., as assignee of the inventors Hallinan, et al.

U.S. Pat. No. 5,817,869, entitled, "Use of Pentavalent Group VA Oxides in Acetic Acid Processing", and issued Oct. 6, 1998, to Quantum Chemical Corporation, as assignee of the inventors Hinnenkamp, et al.

U.S. Pat. No. 5,932,764, entitled, "Iridium-Catalyzed Carbonylation Process for the Production of a Carboxylic Acid", and issued Aug. 3, 1999, to BP Chemicals Limited, as assignee of the inventors Morris, et al.

In the event of conflict between one or more of the incorporated patents and the present disclosure, the present specification, including definitions, controls.

DESCRIPTION CLOSING

This concludes the detailed description. The particular embodiments disclosed above are illustrative only, as the claimed subject matter may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

We claim:

1. A process for producing acetic acid in an acetic acid production system comprising the steps of:
   (i) producing acetic acid in a reactor, wherein the producing step includes a reaction comprising carbon monoxide and methanol in the presence of a catalyst and hydrogen iodide;
   (ii) forming a complex downstream of the reactor by continually introducing a complexing agent into the system downstream of the reactor, wherein the complexing agent comprises a phosphine oxide, wherein the complexing agent is introduced in an amount from about 0.1 to 10 mol per mol of hydrogen iodide, and wherein the phosphine oxide and hydrogen iodide interact to form the complex, and
   (iii) recovering the complex, wherein the catalyst comprises a rhodium catalyst or an iridium catalyst.

2. The process of claim 1 wherein the complexing agent is continually introduced as an acetic acid solution.

3. The process of claim 1 wherein the complexing agent comprises a catalyst stabilizer.

4. The process of claim 3 wherein the catalyst stabilizer comprises triphenylphosphine oxide.

5. The process of claim 1 wherein the complexing agent is introduced upstream of the purification area.

6. The process of claim 1 wherein the phosphine oxide is triphenylphosphine oxide.

7. The process of claim 1 wherein the acetic acid production system comprises a drying column, the process further comprising continually introducing the complexing agent upstream of the drying column.

8. The process of claim 1 wherein the acetic acid production system comprises a reactor, the process further comprising continually introducing the complexing agent into the reactor.

9. The process of claim 1 wherein the acetic acid production system comprises a reactor and a stream in fluid communication with the reactor, the process further comprising continually introducing the complexing agent into the stream.

10. The process of claim 1 wherein the acetic acid production system comprises a flash vessel, the process further comprising continually introducing the complexing agent into the flash vessel.

11. The process of claim 1 wherein the acetic acid production system comprises a flash vessel and a stream in fluid communication with the flash vessel, the process further comprising continually introducing the complexing agent into the stream.

12. The process of claim 1 wherein the acetic acid production system comprises a light-ends column, the process further comprising continually introducing the complexing agent into the light-ends column.

13. The process of claim 1 wherein the acetic acid production system comprises a light-ends column and a stream in fluid communication with the light-ends column, the process further comprising continually introducing the complexing agent into the stream.

14. The process of claim 1 wherein the acetic acid production system comprises a drying column, the process further comprising continually introducing the complexing agent into the drying column.

15. The process of claim 1 wherein the acetic acid production system comprises a drying column and a stream in fluid communication with the drying column, the process further comprising continually introducing the complexing agent into the stream.

16. The process of claim 1 wherein the acetic acid production system comprises a recycle stream, the process further comprising continually introducing the complexing agent into the recycle stream.

17. The process of claim 1 wherein acetic acid production system comprises a reaction mixture comprising water in a concentration of from about 0.2% to about 10% by weight.

18. The process of claim 1 wherein the complexing agent is introduced into the system in an amount based upon a rate of attrition of the complexing agent from a reactor in the system.

* * * * *